United States Patent
Zhai et al.

(10) Patent No.: US 9,824,442 B2
(45) Date of Patent: Nov. 21, 2017

(54) VIEW DIRECTION ADAPTIVE VOLUME ULTRASOUND IMAGING

(71) Applicant: Siemens Medical Solutions USA, Inc., Malvern, PA (US)

(72) Inventors: Liang Zhai, Castro Valley, CA (US); Henry Pavy, Cupertino, CA (US); Bimba Rao, San Jose, CA (US); Bruce A. McDermott, Bellevue, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 104 days.

(21) Appl. No.: 14/831,683

(22) Filed: Aug. 20, 2015

(65) Prior Publication Data

US 2017/0053396 A1  Feb. 23, 2017

(51) Int. Cl.
*G06T 7/00* (2017.01)
*G06T 15/08* (2011.01)
*A61B 8/08* (2006.01)
*A61B 8/00* (2006.01)

(52) U.S. Cl.
CPC .......... *G06T 7/0012* (2013.01); *A61B 8/4483* (2013.01); *A61B 8/461* (2013.01); *A61B 8/467* (2013.01); *A61B 8/483* (2013.01); *A61B 8/54* (2013.01); *G06T 15/08* (2013.01); *G06T 2200/08* (2013.01); *G06T 2207/10136* (2013.01); *G06T 2207/30004* (2013.01)

(58) Field of Classification Search
CPC ........ G06T 7/0012; A61B 8/461; A61B 8/483
See application file for complete search history.

(56) References Cited

U.S. PATENT DOCUMENTS

| | | | |
|---|---|---|---|
| 6,511,426 B1 | 1/2003 | Hossack et al. | |
| 6,544,178 B1 | 4/2003 | Grenon et al. | |
| 7,601,121 B2 | 10/2009 | Pagoulatos et al. | |
| 7,604,595 B2 | 10/2009 | Steen et al. | |
| 8,206,305 B2 | 6/2012 | Garbini et al. | |
| 8,425,422 B2 | 4/2013 | Srinivasan et al. | |
| 8,449,467 B2 | 5/2013 | Wilser et al. | |
| 2009/0054778 A1 | 2/2009 | Pagoulatos et al. | |
| 2010/0056921 A1* | 3/2010 | Rafter | A61B 8/06 600/447 |
| 2012/0289835 A1* | 11/2012 | Hwang | G01S 7/52047 600/447 |
| 2013/0090560 A1* | 4/2013 | Kotaki | A61B 8/14 600/443 |
| 2016/0063742 A1* | 3/2016 | Steen | G06T 5/002 382/275 |
| 2016/0140730 A1* | 5/2016 | Falahatpisheh | G01S 15/8984 382/131 |
| 2016/0350962 A1* | 12/2016 | Steen | G06T 15/08 |

* cited by examiner

*Primary Examiner* — Oneal R Mistry

(57) ABSTRACT

For volume ultrasound imaging, the view direction for rendering a volume image is used. In one approach, imaging parameters for acquiring the volume data prior to rendering are set based on the view direction. For the resolution example, the data for imaging is acquired with the resolution in a view plane greater than resolution along the ray tracing direction. In another approach, sets of data representing a volume are acquired or formed with different settings. The sets are weighted based on the view direction and combined. For the resolution example, an image rendered from the combined data may have greater resolution in the view plane where the set of data with greater resolution in that view plane is weighted more in the combination.

13 Claims, 3 Drawing Sheets

VIEW DIRECTION ADAPTIVE VOLUME ULTRASOUND IMAGING

BACKGROUND

The present embodiments relate to volume imaging in ultrasound. When imaging with ultrasound, due to various constraints and considerations, compromises in imaging are often made to satisfy certain requirements. The compromises tradeoff between detail resolution, contrast, signal-to-noise ratio (SNR), frame rate, penetration, and/or field of view. During volume imaging, the requirement of a sufficient volume rate and/or the physical design of the acoustic array often demand a trade-off between resolution in azimuth and elevation. This results in either mediocre resolution in azimuth and elevation or results in highly anisotropic detail resolution in these two dimensions. In the first scenario, the resolution in both dimensions may not be good enough. In the latter scenario, the dramatic resolution difference between the two dimensions may be very undesirable, especially when the user is rotating the volumes for viewing from different directions. To improve resolution, other undesired tradeoffs are made.

BRIEF SUMMARY

By way of introduction, the preferred embodiments described below include methods and systems for volume ultrasound imaging. The view direction for rendering a volume image is used to assist in the tradeoff. In one approach, imaging parameters for acquiring the volume data prior to rendering are set based on the view direction. For the resolution example, the data for imaging is acquired with the resolution in a view plane greater than resolution along the ray tracing direction. In another approach, sets of data representing a volume are acquired or formed with different settings. The sets are weighted based on the view direction and combined. For the resolution example, an image rendered from the combined data may have greater resolution in the view plane where the set of data with greater resolution in that view plane is weighted more in the combination.

In a first aspect, a method of volume ultrasound imaging is provided. An ultrasound system acquires first and second sets of ultrasound data representing a volume of a patient. The first set has a greater azimuth resolution and lesser elevation resolution than the second set. A view direction for rendering an ultrasound image is received. The ultrasound system weights the first set relative to the second set. The weighting is a function of the view direction. The first and second sets as weighted are combined, and the ultrasound image is generated from the combination of the first and second sets.

In a second aspect, a system is provided for volume ultrasound imaging. A beamformer controller is configured to cause transmit and receive beamformers to scan, with a transducer, a volume of a patient with a setting for at least one parameter different for different representations of the volume in a same mode. A renderer is configured to generate an image of the patient from a weighted combination of the different representations of the volume. A display is configured to display the image.

In a third aspect, a method is provided for volume ultrasound imaging. A view angle relative to a volume of a patient is received. An imaging parameter is set as a function of the view angle. The imaging parameter is for scanning or processing prior to rendering. An ultrasound system acquires ultrasound data representing the volume of the patient. The ultrasound data is acquired with the imaging parameter set as the function of the view angle. An ultrasound image of the patient is rendered from the ultrasound data using the view angle.

The present invention is defined by the following claims, and nothing in this section should be taken as limitations on those claims. Further aspects and advantages of the invention are disclosed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Adaptive volume ultrasound imaging is provided. The imaging adapts to the view direction. In one embodiment, volumes with different resolution distributions are compounded to achieve better details in the resultant volume. In another embodiment, a volume is acquired with settings based on the view direction. Better data for rendering is acquired, and/or multiple datasets are combined to create better data. When balancing imaging characteristics, such as contrast, resolution, imaging depth, and so on, to meet certain imaging requirements, such as the frame rate, using the better data may result in less compromise. To achieve optimal imaging under certain constraints, image acquisition and processing are adaptively adjusted, multiple volumes with system parameters optimized for resolving different aspects of the object are acquired, or both.

In one approach, images are generated with different sets of imaging parameters, such as transmit and receive aperture sizes, imaging frequencies, line density, spatial filters, dynamic range, and so on. The imaging parameters are set based on the view angle of the generated image, so that the volume image presented to the user may be optimal.

In another approach, the imaging system acquires more than one volume with different sets of imaging parameters. Each set of imaging parameters are optimized for certain aspects of the image, such as azimuth and elevation resolution sets. These volumes may be acquired separately with different transmit and receive parameters or acquired using the same transmit operation but formed with different receive parameter settings. View direction-weighted compounding is used to combine these volumes so that the user is presented with an optimal image.

Figure 1:
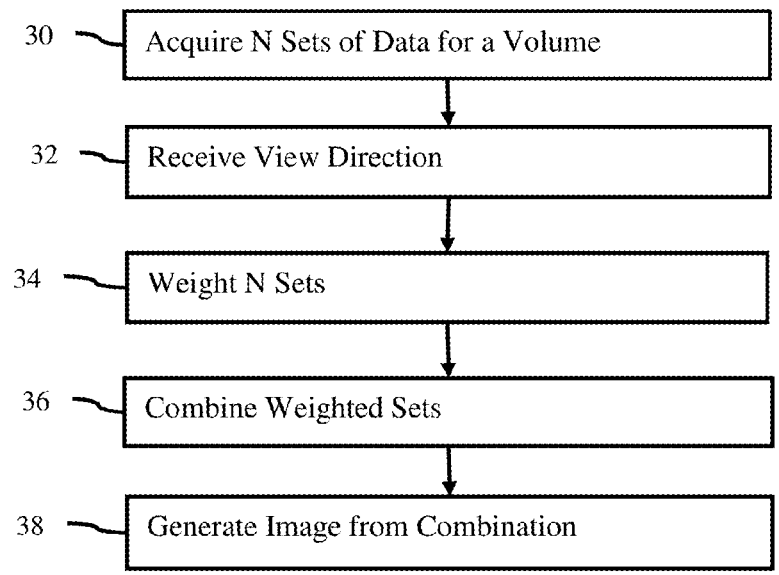
FIG. 1 is a flow chart diagram of one embodiment of a method for volume ultrasound imaging with weighted combination using view direction.

FIG. 1 shows one embodiment of a method of volume ultrasound imaging. In general, different sets of data representing a same volume are acquired. Any number of sets may be acquired, but an example with two sets is used below. Each set has different characteristics, such as different anisotropic resolutions. By weighted combination of the sets, the resulting set representing the volume has the desired characteristics relative to view direction more strongly weighted. The weighting is performed as a function of the viewing direction so that the set with the more desired characteristics relative to the view plane is emphasized.

Figure 6:
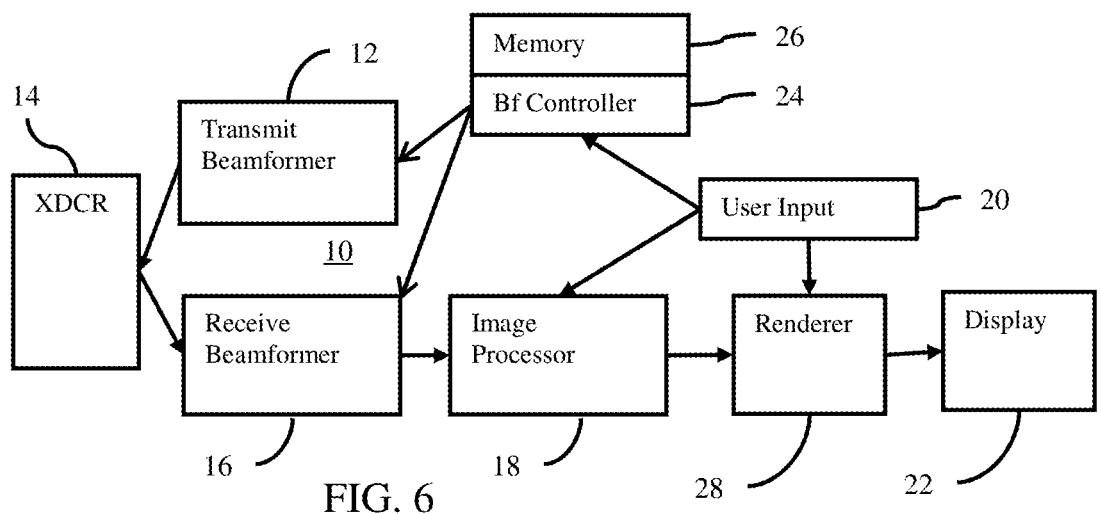
FIG. 6 is a block diagram of one embodiment of a system for volume ultrasound imaging.

The method is performed by the system shown in FIG. 6 or a different system. For example, a medical diagnostic ultrasound imaging system performs act 30-38. More particularly, a beamformer, network interface, or memory is used to acquire in act 30. A processor (e.g., controller, image processor, or renderer) receives the view direction in act 32, weights in act 34, and combines the weighted sets in act 36. A renderer generates the image in act 38. Any of the acts may be performed by other devices.

The acts are performed in the order shown or another order. For example, act 32 is performed before, after, or simultaneously with act 30.

Additional, different or fewer acts may be used. For example, act 38 is not performed. As another example, acts 30-38 are repeated over time for real-time volume imaging. Act 32 may not be repeated in one or more iterations. Acts 32-38 may be repeated without repeating act 30.

In act 30, a plurality of sets of ultrasound data representing a volume of a patient is acquired. The sets are acquired by different scanning. Alternatively, the sets are acquired by different image processing of already acquired data. In yet other embodiments, the sets are acquired by loading the sets from memory or transfer from a network.

In one embodiment, an ultrasound system scans a volume of a patient. The scan is of an entire volume field of view, such as with scan lines distributed in elevation and azimuth to any depth along an axial dimension. The volume is a field of view established by the scanning or configuration. The lateral extent and depth define the extent of the scanned volume. Based on different settings, different size volumes may make up the scan volume. The user or the system determines the field of view and resulting scan volume.

To scan a field of view with ultrasound, transmit and receive beams are formed by an ultrasound system. Any scan format, such as sector, linear, or Vector®, and corresponding field of view may be used. The scanning is of a three-dimensional region or a volume. The scan lines are distributed by electric and/or mechanical steering in three-dimensions, providing data representing a volume (e.g., volume of N×M×R, where N, M, and R are integers greater than 1). Any three-dimensional format may be used, such as scanning sequentially along planes such that the scan planes together represent the volume.

Through receive beamformation, the responsive data represents samples in the field of view. Data received from the scanning is detected. A B-mode detector determines the intensity of acoustic echoes represented by the received data. For example, the receive data is formatted as in-phase and quadrature data. A square root of a sum of the squares of the in-phase and quadrature terms is calculated as the intensity. Other measures of the magnitude of the acoustic echo may be used for B-mode detection.

Other processing may be performed based on values for parameters. For example, the detected B-mode data is spatially filtered. The kernel, cut-off frequency, type of filter or other characteristic may vary as a function of direction. As another example, a sequence of frames from a corresponding sequence of scans of the entire field of view is acquired. Different pairs or other sized groupings of the resulting B-mode frames of data are temporally filtered. Infinite impulse or finite impulse response filtering may be used. In another example, a general or overall gain is applied. One or more parameters may establish the overall gain. Additionally or alternatively, depth dependent gains may be applied. Different, additional, or fewer processing parameters may be used, such as dynamic range.

In other embodiments, other types of detection and corresponding scans are performed. For example, color flow (e.g., Doppler) estimation is used. Velocity, power, and/or variance are estimated. As another example, harmonic mode is used, such as imaging at a second harmonic of a fundamental transmit frequency. Combinations of modes may be used.

After processing, the detected data is scan converted, if needed. A two-dimensional image may be generated. For example, a B-mode image represents the intensity or strength of return of acoustic echoes in the B-mode field of view. The intensities or B-mode data is mapped to gray scale within the dynamic range of the display. The gray scale may be equal or similar red, green, blue (RGB) values used by the display to control pixels. Any color or gray scale mapping may be used. The detected data, before or after display mapping, may be converted to a three-dimensional grid, such as interpolating from the scan format or from scan converted data.

Data used for other acts is from any point in the processing path. In one embodiment, detected and scan converted scalar values are used prior to any color or display mapping. In other embodiments, beamformed samples prior to detection, detected data before scan conversion, or display values after display mapping are used.

The data of the two or more sets representing the volume have different characteristics. The differences may be in resolution, contrast, signal-to-noise ratio, penetration, and/or other characteristics. For example, the differences are in resolution. In one embodiment, one set of data has a greater azimuth resolution and lesser elevation resolution than another set. The azimuth resolution in the one set may be the same or different from the elevation resolution of the other set, and the elevation resolution in the one set may be the same or different from azimuth resolution in the other set.

The transmit and/or receive beam characteristics may be set or responsive to values of parameters. The depth and/or lateral extent of the field of view is set. Similarly, the transmit beam focal depth, transmit frequency, receive frequency, line density, sampling density, transmit waveform (e.g., number of cycles and/or envelope shape), frame rate, aperture size (e.g., number of elements), and/or other scanning characteristics are set. The number of transmit focal positions per scan line (e.g., one or two) may be set. Different, additional, or fewer scan (e.g., transmit and/or receive) parameters may be used.

The differences in characteristic are created by different scanning and/or image processing by the ultrasound system. Imaging parameters for acquiring the ultrasound data are different for the different sets of data representing the volume. Example imaging parameters include post-scanning processing parameters, such as spatial or temporal filtering.

Other example imaging parameters include scan parameters used for transmit and/or receive beamforming.

The difference is between sets and/or between dimensions within a given set. By providing different spatial distribution within a set, different sets may have different characteristics, such as one set providing lesser resolution along one dimension but greater resolution along another dimension than another set. The differences are along azimuth and/or elevation for each of the sets, and/or the different values are different between the different sets.

In one embodiment, a different focus and/or line density is provided for the sets. For example, the line density is greater and the focus narrower for scan lines distributed along azimuth in one set than for another set. The line density is greater and the focus narrower for scan lines distributed along elevation in the other set than for the one set. Greater line density and/or tighter focus may provide better resolution, while lesser line density and/or broader focus may improve frame rate.

In another embodiment, an aperture size is different for the different sets. The transmit and/or receive aperture is different between the sets and/or between different dimensions within the set. For example, an aperture size is greater along azimuth for one set than the other set and greater along elevation for other set than the one set. A larger or greater apertures size may result in greater resolution.

Other imaging parameters for which different settings result in sets of data with different characteristics include a number of receive beams formed for each transmit beam (e.g., receive one beam for each transmit beam versus receive four or more beams for each transmit beam), spatial filtering (e.g., greater or lesser amounts, different cut-off frequencies, or other filtering characteristics), and/or apodization profile.

Yet another imaging parameter is coherent beamformation along a fast scan direction. The fast scan direction is the dimension along which sequential beams are immediately acquired, such as azimuth where the three-dimensional scan pattern is along azimuth scan lines for one elevation plane before scanning a different elevation plane. Scan line or beam interpolation, retrospective focusing, or other beam processing using phase information may be applied differently as a function of dimension within a set and/or between sets.

Different settings for any combination of imaging parameters may be used. One or more of the imaging parameters may have a same setting for acquiring the data of the different sets.

Figure 2:
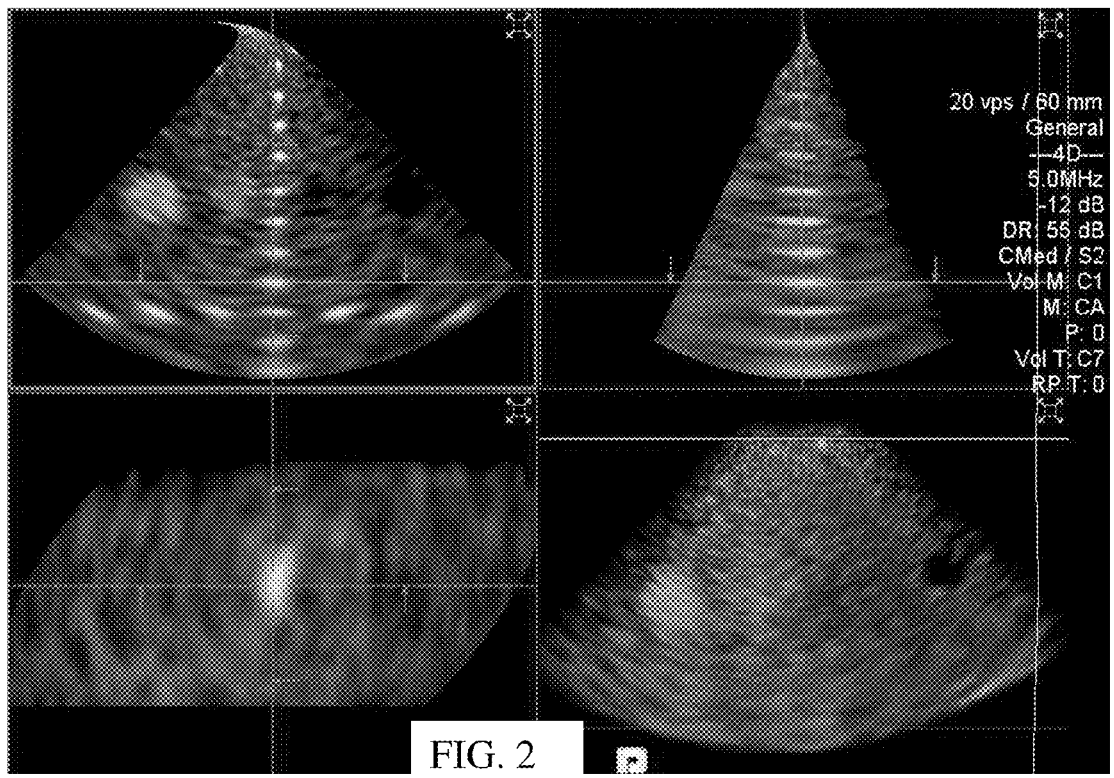
FIG. 2 is an example multi-planar view of a volume from data having greater azimuth resolution than elevation resolution.
Figure 3:
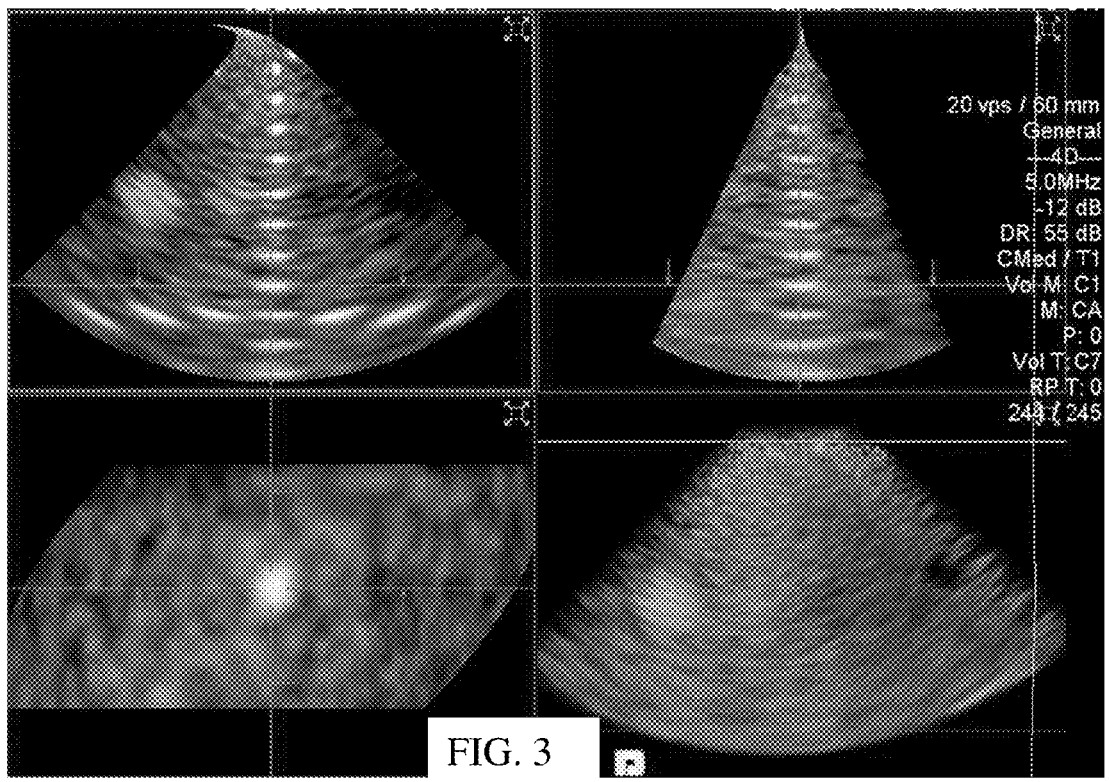
FIG. 3 is an example multi-planar view of a volume from data having greater elevation resolution than azimuth resolution.

FIGS. 2 and 3 show example multi-planar images for different sets representing a same volume. Images are generated for three orthogonal planes through the volume for each set. The lower-left image is a c-plane or azimuth-elevation plane perpendicular to the axial dimension. The upper-left image is of an azimuth-axial plane perpendicular to the elevation dimension. The upper-right image is of an elevation-axial plane perpendicular to the azimuth dimension. The lower-right image is a three-dimensional rendering of the volume from a viewing direction along the elevation axis. The graphic lines indicate the relative geometric locations of these imaging planes. Other plane positioning and/or view directions may be used.

The azimuth resolution for one set is greater than the other set. The elevation resolution for the other set is greater than the one set. In this example, the volume is scanned with a twisted array (e.g., see U.S. Pat. Nos. 8,206,305 and 8,449,467) having elements rotated around the azimuthal axis, such as in a helical pattern. Different elements along the azimuth face different directions. The twist is used to create or increase the field of view in elevation so that the array may be used for volume imaging. By walking the aperture along the azimuth, the imaging plane is centered at different elevation directions.

When imaging with these arrays, a compromise in resolution is made between the azimuth and elevation resolution. A good azimuthal resolution requires large enough active transmit and/or receive aperture sizes. However, because elements at different azimuthal locations are facing different directions, a larger azimuth aperture produces worse elevation resolution. Smaller azimuth aperture size may result in less azimuth resolution, but greater elevation resolution.

In FIG. 2, the image is well focused in the azimuth (see upper-left image), but is blurry in the elevation (see upper-right image). The lower-left image shows a high azimuth-elevation aspect ratio of the resolved pin target, which is supposed to be uniform in both dimensions. By decreasing the azimuthal receive aperture size, the elevation resolution may be noticeably improved as shown in FIG. 3. However, the azimuthal resolution is degraded (i.e., compare the upper-left images of FIG. 2 (better azimuth resolution) and FIG. 3 (degraded azimuth resolution)).

The values of the parameters are initially set using any process. In one embodiment, one or more of the parameters are set based on input by the user, predetermined values, and/or selection of an application or configuration. For example, the user selects volume or three-dimensional imaging of a particular anatomy. In alternative or additional embodiments, one or more of the parameters are set based on feedback or adapting to the data received from the scanning. Automatic setting of the value or values of the parameter or parameters is performed. For example, the overall gain and/or dynamic range of B-mode data is set based on identifying B-mode data for locations associated with tissue in the field of view and using an average, median or other B-mode intensity for the tissue locations to set the gain and/or dynamic range.

During live or real-time imaging (scanning and outputting images at the same time or while the patient has a transducer placed against them), no special interaction is generally required or expected of the user. The user may select only an application (e.g., three-dimensional imaging of anatomy) and the remaining configuration automatically occurs. The user may pre-configure any one or more of the settings and then the imaging occurs without further change by the user. In other embodiments, configurability of the volume imaging is still available during the live imaging. The user may alter one or more values of scan parameters without being required or expected to alter as part of the normal workflow.

The different sets of data are acquired using different scans, including different transmit and receive operations. Since multiple sets are acquired to form an image, the frame rate may be reduced. In another embodiment, the same transmit beams are used for the different sets, but different receive beamformation (i.e., receive scan parameters) and/or different post-beamforming (e.g., different spatial filtering) are provided. Using the same transmit beams with different settings for receive beamformation for multiple sets of data avoids a reduction in frame rate yet still provides data sets with different characteristics. For example, two different sets or frames of data are simultaneously formed by using two different receive aperture sizes or aperture functions so that one set is optimized for azimuth and the other set for elevation. The receive parameters with different settings may be any, such as aperture size, apodization, or frequency bands. Where the difference is post scan, the same receive samples are used to create the two sets of data with different characteristics at the scan frame rate, such as using different filtering and/or dynamic range.

The type of scan or image process, such as the mode of scanning, is the same for the different sets of data. For example, harmonic imaging is used for all of the sets.

Referring again to FIG. 1, a view direction is received by a renderer, processor, user input, or other component of the ultrasound system in act 32. The view direction is a direction along which an image is to be rendered or viewed. The view direction is parallel or substantially parallel ("substantially" used to account for divergence of rays) to the ray casting used in volume rendering or an orthogonal line to a view plane. The angle of a line relative to the volume is the view direction. In the example of FIGS. 2 and 3, the view direction for the three-dimensional rendering is parallel to the elevation axis.

The view direction is set, predetermined, or a default value. Alternatively, the user inputs the view direction. For example, the user inputs a starting view direction or a change in view direction. The view direction may change over time, such as where the imaged volume appears to rotate over time or where the user causes the imaged volume to rotate relative to the viewer.

In acts 34 and 36, the different sets (e.g., N sets where N is an integer greater than one) are combined in a weighted combination. A filter or processor combines the samples or voxels for the same locations from the different sets.

In act 34, the ultrasound system relatively weights the sets for the weighted combination. Voxels or intensities representing the same locations are relatively weighted. The same weights are applied to all the voxels of given set of data. In other embodiments, the weights vary as a function of location. Different weights are applied to the different sets, weighting one set more than another. For equal weighting, the weights of the different sets may be the same.

The weighting is relative. All the sets are weighted. Alternatively, fewer than all the sets are weighted (e.g., one or more sets have a weighting of one). The weights are values between or including 0-1. In other embodiments, weights greater than one may be used.

The weighting emphasizes one or more sets as compared to others based on the view direction. The view direction is mapped to the weights for the different sets using equations and/or look-up tables. The weighting is used to combine the sets so that the displayed image may be optimal for the image. In the example where each of the two sets has different azimuth and elevation resolutions, the weighting emphasizes the set with the better resolution relative to the view direction.

For example, where the view direction is along the elevation axis, the set of data with greater resolution in azimuth is emphasized. Where the view direction is at a 45-degree angle to azimuth and elevation, both sets may be equally weighted. Where the view direction is along the azimuth axis, the set of data with greater resolution in elevation is emphasized. For angles in between, any linear or non-linear mapping of weight to view direction may be used.

As another example, the set of FIG. 2 is more heavily weighted than the set of FIG. 3 where the viewing direction is more orthogonal to an azimuth-axial plane than to an elevation-axial plane, and the set of FIG. 3 is more heavily weighted than the set of FIG. 2 where the viewing direction is more orthogonal to the elevation-axial plane than to the azimuth-axial plane.

In one embodiment, the weighting is a function of a cosine or other trigometric function of the view direction. The normal direction to the azimuth-axial plane defined as 0 degrees, but other directions relative to the volume may be defined as 0 degrees. The voxel in the new volume is computed using: Ouput_voxel(i,j,k)=vol1_voxel(i,j,k)*|cos (alpha)|+vol2_voxel(i, j k)*(1−|cos(alpha)|), where vol1 is a first set (e.g., FIG. 2 set), vol2 is a second set (e.g., FIG. 3 set), (i, j, k) are azimuth, elevation, and axial indexes (i.e., voxel indexes), output_voxel is the combined voxel, and alpha is the view angle from the normal direction of the azimuth-axial plane. Other linear or nonlinear weighting may be used.

When the view direction changes, the weighting is changed. For example, the user rotates the imaged volume about the axial axis, so alpha changes. The weights are recalculated based on the current view direction. Where the same sets are used over time, the resulting combination is of the same sets with altered weights. Where real-time imaging is provided, the altered weights are applied to the most recently acquired sets with different characteristics.

In act 36, the processor, renderer, or other component of the ultrasound system combines the weighted sets. Weighted averaging of the voxels representing the same locations is performed. For each location, a weighted average of the voxels from the two sets for that location provides the combined voxel for that location. For example, the cosine (alpha) weighting is used for summing the weighted results, providing output_voxel (i, j, k) as the combined voxel value. By repeating for different locations, a combined data set representing the volume from a combination of data sets with different characteristics is formed.

Any linear or nonlinear function may be used to combine the sets. For example, a maximum or minimum selection (e.g., binary weights) may be used. In another embodiment, the combination is of pixels from rendered images rather than voxels.

Figure 4:
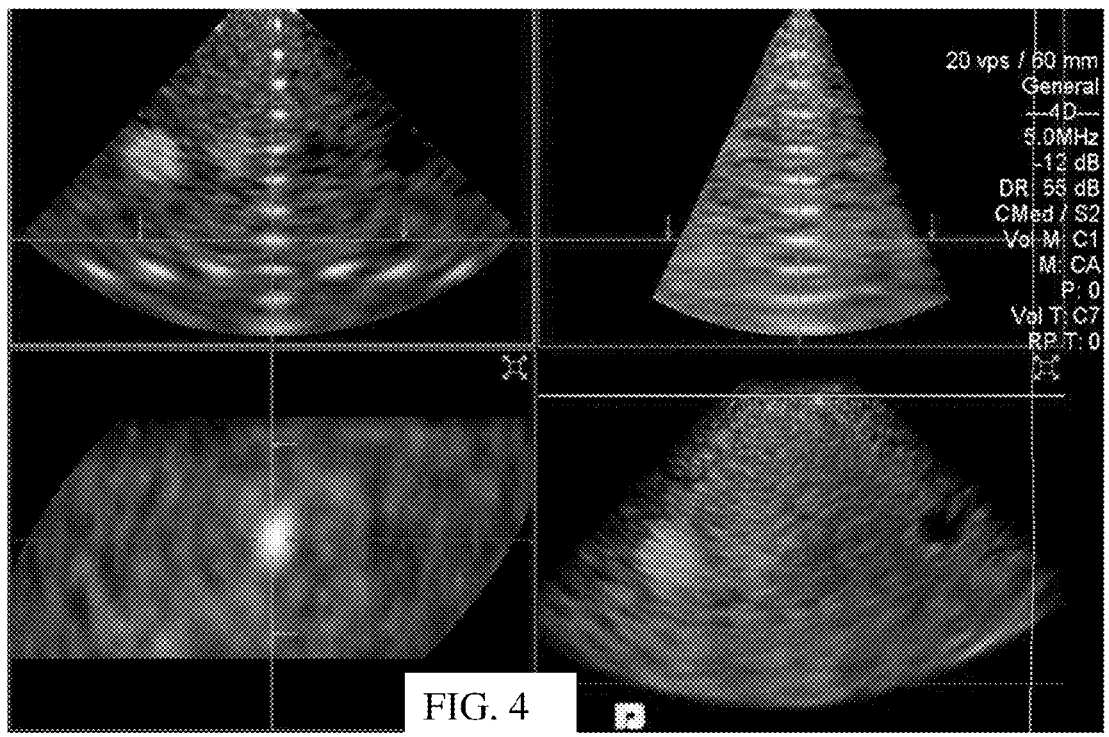
FIG. 4 is an example multi-planar view of a volume from a weighted combination of sets using a view angle for weighting.

FIG. 4 shows a multi-planar reconstruction from a combined set form the sets of FIGS. 2 and 3 using the cosine (alpha) weighting. The four panels or images have a same spatial orientation as discussed above for FIGS. 2 and 3. The top two images and lower left image are three orthogonal views, thus are computed with different weights. In the top-left (azimuth-axial) and top-right (elevation-axial) images, alpha equal to 0 and 90 degrees, respectively. Thus, the weight coefficients of the first volume data (FIG. 2) are 1 and 0. The lower-left (azimuth-elevation) image is a simple average (weight coefficient, 0.5) of the same view in FIGS. 2 and 3 as the view angle is perpendicular to the azimuth-elevation plane. The lower-right is a volume projection image calculated based on the view angle by weighting the volumes shown in FIGS. 2 and 3. The user can change the view angle of any of these cut planes or the volume. The weights are updated automatically based on the user's or processor determined view angles. The combination results in improved resolution along one dimension (e.g., along elevation—compare upper-right image of FIGS. 2-4) without loss of much resolution along another dimension (e.g., along azimuth—compare upper-left image of FIGS. 2-4). A more optimal image is presented to the user by the combination. The image is more optimal by accounting for the view direction. The resulting data after combination represents the volume, but with enhanced characteristic relative to no combination or less variation.

The data for one set may be acquired at a different spatial resolution than for the other set, or the data along one dimension for a set may be at a different resolution than the data for the same dimension of another set. For example, one set of data represents the volume at 1.5 times the spatial resolution (e.g., 1.5 line and sample density) than another set along a given dimension. The data of the sets is interpolated spatially to have a matching sample and/or line density. One set is interpolated to a grid of another set or both sets are interpolated to a common grid. The interpolated sets have a dense acoustic grid that matches a highest resolution of the sets along each dimension. The sets along the common grid are used for combination.

In act 38, the ultrasound system, such as a processor or renderer, generates an ultrasound image. One or more images are generated, such as a planar image, a rendering of the volume, or a multi-planar reconstruction. Three-dimensional images are generated with rendering. Any rendering may be used, such as projection or surface rendering. For example, rays are traced along or with minor deviation (e.g., 5% or less) from the view direction through the volume represented by the combination set of data. Minimum, maximum, alpha blending, or other ray projection is used to create a two-dimensional image or pixels representing the volume or three-dimensional distribution of data. Shading may or may not be added.

The image or images are generated using the view direction. For a planar image, the view direction is orthogonal to the plane. For a three-dimensional rendering, the view direction is a direction along which rays are cast or from which the viewer perceives the volume. The view direction is the same as used for weighting. The view direction is fixed or varies over time.

The data acquired in act 30 is used to generate the image. The processor, renderer, or other device generates an image from the combination set representing the volume. For example, the data resulting from weighted combination of two or more sets with different characteristics is passed to a three-dimensional renderer. The different sets may be rendered separately as well or alternatively.

A sequence of images is generated. As the acquisition is repeated, corresponding image generation is also repeated. Newly acquired sets of data representing the volume are used to generate an image. Live imaging updated as the data becomes available is performed. The images are generated at the same or lesser frame rate as the volume scan. Temporal blending or interpolation may be used to increase the display frame rate.

The images are B-mode images, but may be other modes. The imaging is used for diagnosis and/or treatment guidance. In one embodiment, the imaging is minimally disruptive to existing user workflows. The user simply sees significantly improved image quality of the targeted anatomical feature without distraction or extra effort.

Figure 5:
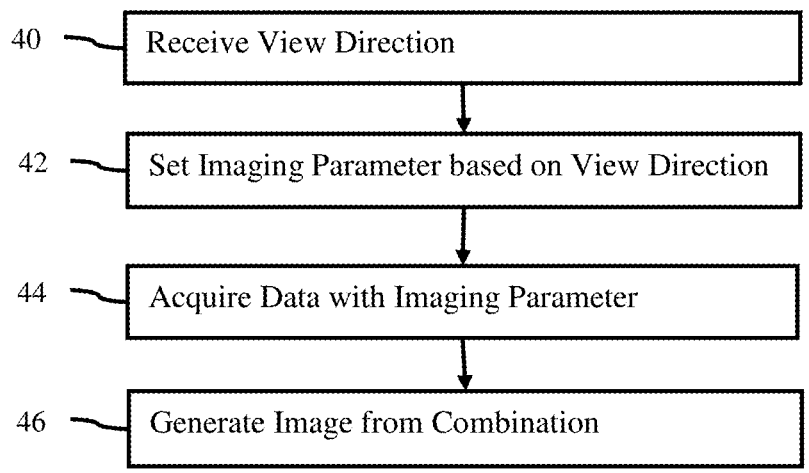
FIG. 5 is a flow chart diagram of one embodiment of a method for volume ultrasound imaging with imaging parameters set based on view angle.

FIG. 5 shows one embodiment of a method of volume ultrasound imaging. Rather than relying on weighted combination of sets with different characteristics, a set of data representing the volume at a given time is acquired with one or more characteristics oriented relative to the view direction. The view direction is used to set one or more imaging parameters so that the resulting set of data is acquired with a desired orientation of the characteristic or characteristics.

The method is performed by the system shown in FIG. 6 or a different system. For example, a medical diagnostic ultrasound imaging system performs act 40-46. More particularly, a beamformer, network interface, or memory is used to acquire in act 44. A processor or controller receives the view direction in act 40 and sets the imaging parameters in act 42. A renderer generates the image in act 46. Any of the acts may be performed by other devices.

The acts are performed in the order shown or another order. Additional, different or fewer acts may be used. For example, act 46 is not performed. As another example, acts 40-46 are repeated over time for real-time volume imaging. Act 40 may not be repeated in one or more iterations.

In act 40, a view angle or direction is received. The view angle is input by the user or loaded from memory as a pre-set or predetermined value. The view angle may be received as discussed above for act 32.

In act 42, one or more imaging parameters are set based on the view angle. The imaging parameter or parameters are set to provide a desired characteristic. The setting is a value for the parameter. The value may be based on a tradeoff, such as setting a value for focus and line density for one dimension resulting in lesser line density and focus for another direction. A baseline of the value may be based on default, imaging application, or other consideration. The baseline is altered based on the view angle. Alternatively, a look-up of the value based on the view angle is used.

The setting is different along elevation than for along azimuth. While the view angle may not be exactly along elevation or azimuth, the imaging (e.g., scan parameters) may vary just along elevation and azimuth. Alternatively, the setting is different along the view angle than for orthogonal to the view angle. Scan parameters and/or post processing parameters may vary in an arbitrary direction, so vary based on the view direction without regard to azimuth or elevation.

Any imaging parameter may be set as a function of the view angle. For example, values for parameters for scanning (e.g., beamforming parameter) and/or parameters for pre-rendering, post-beamforming (e.g., spatial filtering or dynamic range) are set. For example, one or more of aperture size, imaging frequency, line density, spatial filtering, coherent beamforming, or combinations thereof are set. Any of the parameters discussed herein or other parameters may be set to provide a difference in a characteristic as a function of spatial distribution in the set for the volume.

The setting provides for the desired characteristic within the view plane or orthogonal to the view angle. The characteristic is reduced along the view direction in a tradeoff. For example, the resolution in a view plane is set higher using line density than the resolution along the view direction.

Other imaging parameters are set based on other considerations, such as a user selected imaging application, the anatomy being imaged, or default values. All of the parameters are set, but only a sub-set is based on the view angle. Alternatively, all of the parameters are based, at least in part, on the view angle.

In act 44, the ultrasound system acquires ultrasound data representing the volume of the patient. The acquisition is as discussed above in act 30, but only one set of data for a given time or period is acquired. Additional sets for a given time may be acquired.

The acquisition is by scanning. Where a scan parameter is set based on the view angle, the volume is scanned using the setting of the parameter or parameters. Alternatively, the acquisition is by loading from memory or receiving a transfer. Where the parameter is post-scan (e.g., spatial filter), a previously acquired set may be altered by application of the process responsive to the setting of the parameter.

In one embodiment, the set of ultrasound data is acquired with greater resolution along a direction orthogonal to the view angle than parallel with the view angle. Where the view angle is off-axis from the azimuth or elevation, the view angle may be closer to one of the axes. Given a data set acquired with greater resolution along the axis more orthogonal to the view angle, the data may be acquired with greater resolution more orthogonal to the view angle. Alternatively, the resolution is maximized along a plane offset from the cardinal axes. In either case, the acquired data has a character (e.g., resolution) different along the view angle than for orthogonal to the view angle. By having greater resolution orthogonal to the view angle, the resulting image from the view angle may have improved character as opposed to not using the view direction to acquire the data.

In act 46, an ultrasound image is generated from the acquired data. For example, an ultrasound image is rendered from data representing a volume of the patient. The ultrasound image is generated based on the view angle. Any of the image generation discussed above for act 38 may be used.

FIG. 6 shows one embodiment of a system 10 for volume ultrasound imaging. The user configures the system 10 for volume or three-dimensional imaging, such as selecting an application for volume imaging specific anatomy. The user may alter values of one or more presets of parameters as desired. Once acquisition starts, the system 10 acquires data representing the volume with desired characteristics. By combining sets with different characteristics as a function of view direction, an improved data set for imaging from the view direction may result. By acquiring a set of data with a characteristic oriented based on the view direction, an improved data set for imaging from the view direction may result.

The system 10 is an ultrasound imager. In one embodiment, the ultrasound imager is a medical diagnostic ultrasound imaging system. In alternative embodiments, the ultrasound imager is a personal computer, workstation, PACS station, or other arrangement at a same location or distributed over a network for real-time or post acquisition imaging.

The system 10 implements the method of FIG. 1, method of FIG. 5, or other methods. The system 10 includes a transmit beamformer 12, a transducer 14, a receive beamformer 16, an image processor 18, a user input 20, a renderer 28, a display 22, a beamformer controller 24, and a memory 26. Additional, different or fewer components may be provided. For example, the receive beamformer 16 through the display 22 represents a B-mode processing path of an ultrasound imager. Other components may be provided in the path, such as a spatial filter, a scan converter, a mapping processor for setting dynamic range, or an amplifier for application of gain. As another example, the user input 20 is not provided.

The user input 20 is a mouse, trackball, touch pad, touch screen, keyboard, button, slider, knob, sensor, or combinations thereof. The user input 20 is configured to receive a view direction for the render 28, image processor 18, and/or beamformer controller 24. A user interface provides a tool or input selection for the user to set or change the view direction for imaging or as imaging the volume. Alternatively, the view direction is automatically determined or loaded from memory.

The transmit beamformer 12 is an ultrasound transmitter, memory, pulser, analog circuit, digital circuit, or combinations thereof. The transmit beamformer 12 is configured to generate waveforms for a plurality of channels with different or relative amplitudes, delays, and/or phasing to focus a resulting beam at one or more depths. The waveforms are generated and applied to a transducer array with any timing or pulse repetition frequency. For example, the transmit beamformer 12 generates a sequence of pulses for different laterally and/or range regions. The pulses have a center frequency.

The transmit beamformer 12 connects with the transducer 14, such as through a transmit/receive switch. Upon transmission of acoustic waves from the transducer 14 in response to the generated waves, one or more beams are formed during a given transmit event. The beams are for B-mode or other mode of imaging. Sector, Vector®, linear, or other scan formats may be used. The same region is scanned multiple times for generating a sequence of images. The formed beams have an aperture, origin on the transducer 14, and angle relative to the transducer 14. The beams in the field of view have a desired line density and format. A multiplexer, switches, or other device allows selection of a transmit aperture (i.e., position on the array and size).

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. For example, the transducer 14 is a one-dimensional PZT array with about 64-256 elements. "About" accounts for dead or non-functioning elements in the array.

The transducer 14 connects with the transmit beamformer 12 for converting electrical waveforms into acoustic waveforms, and connects with the receive beamformer 16 for converting acoustic echoes into electrical signals. The transducer 14 transmits the waveforms forming the transmit beams where the waveforms have a frequency and are focused at a tissue region or location of interest in the patient. The acoustic waveforms are generated in response to applying the electrical waveforms to the transducer elements. The transducer 14 transmits acoustic energy and receives echoes. The receive signals are generated in response to ultrasound energy (echoes) impinging on the elements of the transducer 14.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission for detection. Dynamic focusing on receive may be provided. The receive beamformer 16 outputs data representing spatial locations using the received acoustic signals. Relative delays and/or phasing and summation of signals from different elements provide beamformation. In alternative embodiments, the receive beamformer 16 is a processor for generating samples using Fourier or other transforms. The sampling density by the receive beamformer 16 is for a range of depths. Timing is used to select the range of depths over which the sampling occurs. The receive beams have a desired scan line density at an orientation or orientations using an aperture. A multiplexer, switches, or other device allows selection of a receive aperture (i.e., position on the array and size).

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental, or other band. The fundamental frequency band may alternatively be used. Alternatively, coherent beamformation is performed by the filter or processor of the receive beamformer 16.

The receive beamformer 16 outputs beam summed data representing spatial locations. Data for locations for a volume are output. Using parallel or sequential processing, the receive beamformer 16 may output different sets of data with different characteristics.

The beamformer controller 24 and/or another processor configure the beamformers 12, 16. The beamformer controller 24 is a processor, application specific integrated circuit, field programmable gate array, digital circuit, analogy circuit, combinations thereof, or other device for configuring the transmit and receive beamformers 12, 16.

The beamformer controller 24 may use the memory 26 to acquire and/or buffer values for different beamformer parameters. The values may be accessed by the beamformers 12, 16 and/or loaded from the memory 26 into buffers of the beamformers 12, 16 to configure the beamformers 12, 16. By loading values into registers or a table used for operation, the values of acquisition parameters used by the beamformers 12, 16 for three-dimensional imaging are set. Any control structure or format may be used to establish the imaging sequence. The beamformers 12, 16 are caused to acquire data for three-dimensional imaging at a frame rate, with a transmit focus, at an imaging frequency band, over a depth, with a line density, at a sample density, with transmit and receive apertures, and/or at line orientation. Different values of one or more acquisition or scanning parameters may result in a different frame rate, signal-to-noise ratio, penetration, contrast and/or resolution. One or more of the parameters may be set based on the view angle. Alternatively, one or more of the parameters may be set based on the set being acquired (i.e., different settings for acquiring different sets) and/or as a function of the spatial location (e.g., different for different axes).

The beamformer controller 24 causes the beamformers 12, 16 to scan a volume of a patient. Any three-dimensional scan format may be used. The beamformer controller 24 configures the beamformers 12, 16 to interleave scanning of the volume to acquire different sets with different characteristics. Alternatively, receive operation to form different sets from the same transmit operations are performed in parallel. The volume is scanned with a setting or settings for at least one parameter being different for different representations of the volume. The different representations are scanned for a same imaging mode (e.g., B-mode). For example, beamformed samples for two sets of data to be used in B-mode imaging are acquired by scanning where the different representations have different resolutions along different directions relative to the volume and/or each other. In other embodiments, the beamformer controller 24 configures the beamformers 12, 16 to acquire a set based on the view direction.

The image processor 18 detects, such as detecting intensity, from the beamformed samples. Any detection may be used, such as B-mode and/or color flow detection. In one embodiment, a B-mode detector is a general processor, application specific integrated circuit, or field programmable gate array. Log compression may be provided by the B-mode detector so that the dynamic range of the B-mode data corresponds to the dynamic range of the display. The image processor 18 may or may not include a scan converter.

The image processor 18 may perform spatial filtering and/or dynamic range setting. Different filtering and/or dynamic range are applied along different directions and/or between different representations (e.g., sets) of the volume.

The image processor 18 may perform weighted combination of different sets. The weights as a function of view direction are calculated or looked up and applied to the different representations. The weighted representations are averaged or combined. In alternative embodiments, the renderer 28 performs the weighted combination. Alternatively, weighted combination is not performed where the data is acquired based on the view angle.

The renderer 28 is a graphics processing unit, graphics card, separate computer, processor, or other device for three-dimensional rendering. The renderer 28 is configured by software, hardware, and/or firmware to generate an image or images of the patient from the acquired set or combination set of ultrasound data. Separate images for different planes may be generated. Different images may be generated using a same view direction or data combined based on one view direction. Alternatively, different images are generated from different weighted combinations to account for different view directions for each image. A sequence of such images may be generated.

The display 20 is a CRT, LCD, monitor, plasma, projector, printer, or other device for displaying one or more images or a sequence of images. Any now known or later developed display 20 may be used. The display 20 displays three-dimensional representations, images representing a plane or planes, and/or multi-planar reconstructions. The display 20 displays one or more images representing the volume.

The spatial resolution and/or image quality is based, in part, on the view direction. By weighting based on view direction, the resulting image from the combination may have more desired resolution or other characteristic. By acquiring based on view direction, the resulting image may have more desired resolution or other characteristic.

The beamformer controller 24, image processor 18, renderer 28, other processor, and/or the ultrasound system 10 operate pursuant to instructions stored in the memory 26 or another memory. The instructions configure the system for performance of the acts of FIG. 1 or FIG. 5. The instructions configure for operation by being loaded into a controller, by causing loading of a table of values, and/or by being executed. The memory 26 is a non-transitory computer readable storage media. The instructions for implementing the processes, methods and/or techniques discussed herein are provided on the computer-readable storage media or memories, such as a cache, buffer, RAM, removable media, hard drive, or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method of volume ultrasound imaging, the method comprising:
acquiring, with an ultrasound system, first and second sets of ultrasound data representing a volume of a patient, the first set having a greater azimuth resolution and lesser elevation resolution than the second set;
receiving a view direction for rendering an ultrasound image;
weighting, by the ultrasound system, the first set relative to the second set, the weighting being a function of the view direction;
combining the first and second sets as weighted; and
generating the ultrasound image from the combination of the first and second sets.

2. The method of claim 1 wherein acquiring comprises scanning the volume, the azimuth and elevation resolutions being based on settings of scan parameters of the ultrasound system.

3. The method of claim 2 wherein a focus is narrower along azimuth for the first set than the second set and narrower along elevation for the second set than the first set.

4. The method of claim 2 wherein a line density is greater along azimuth for the first set than the second set and greater along elevation for the second set than the first set.

5. The method of claim 2 wherein an aperture size is greater along azimuth for the first set than the second set and greater along elevation for the second set than the first set.

6. The method of claim 2 wherein the scanning has different values for a number of receive beams formed for each transmit beam, spatial filtering, and/or apodization profile along azimuth and elevation for each of the first and second sets, and the different values being different between the first and second sets.

7. The method of claim 1 wherein receiving the viewing direction comprises receiving the viewing direction from a user input.

8. The method of claim 1 wherein weighting comprises weighting as a function of a cosine of the viewing direction.

9. The method of claim 1 wherein combining the first and second sets as weighted comprises weighted averaging voxels of the first set with voxels of the second set, the averaging being of voxels of the first set representing same locations as the voxels of the second set.

10. The method of claim 1 wherein generating comprises volume rendering as a function of the view direction.

11. The method of claim 1 wherein generating comprises ray tracing along the view direction through the combination representing the volume.

12. The method of claim 1 wherein acquiring comprises using a same set of transmit beams for both the first and second sets and different settings for receive beamformation.

13. A method of volume ultrasound imaging, the method comprising:
acquiring, with an ultrasound system, first and second sets of ultrasound data representing a volume of a patient, the first set having a greater azimuth resolution and lesser elevation resolution than the second set;
receiving a view direction for rendering an ultrasound image;
weighting, by the ultrasound system, the first set relative to the second set, the weighting being a function of the view direction, weighting the first set more heavily than the second set where the viewing direction is more orthogonal to an azimuth-axial plane than to an elevation-axial plane and weighting the second set more heavily than the first set where the viewing direction is more orthogonal to the elevation-axial plane than to the azimuth-axial plane;
combining the first and second sets as weighted; and
generating the ultrasound image from the combination of the first and second sets.

* * * * *